(12) United States Patent
Cohen

(10) Patent No.: US 6,677,157 B1
(45) Date of Patent: Jan. 13, 2004

(54) METHOD OF DIAGNOSIS OF PROSTATE CANCER

(75) Inventor: Ronald Joseph Cohen, Dianella (AU)

(73) Assignee: Uropath Pty Ltd., A.C.N., Nedlands (AU)

( * ) Notice: Subject to any disclaimer, the term of this patent is extended or adjusted under 35 U.S.C. 154(b) by 0 days.

(21) Appl. No.: 09/786,090

(22) PCT Filed: Aug. 30, 1999

(86) PCT No.: PCT/AU99/00698

§ 371 (c)(1),
(2), (4) Date: May 9, 2001

(87) PCT Pub. No.: WO00/11947

PCT Pub. Date: Mar. 9, 2000

(30) Foreign Application Priority Data

| Aug. 28, 1998 | (AU) | PP5549 |
| Jun. 4, 1999 | (AU) | PQ0784 |

(51) Int. Cl.⁷ .............................................. A61K 31/11
(52) U.S. Cl. ...................................................... 436/63
(58) Field of Search ............................... 424/93.7, 93.1; 435/325, 410, 252.1, 260; 436/63; 514/693

(56) References Cited

U.S. PATENT DOCUMENTS

| 3,997,656 A | 12/1976 | Wertlake et al. ................ 424/3 |
| 4,404,181 A | 9/1983 | Mauthner ....................... 424/3 |

FOREIGN PATENT DOCUMENTS

| EP | 99944166 | 10/2002 |
| IE | 78909 | 3/1998 |
| WO | WO 92/10935 | 7/1992 |
| WO | WO 92 10935 | * 7/1992 |
| WO | WO 99/24026 | * 5/1999 |

OTHER PUBLICATIONS

Gaudin et al. (American J. Clin. Path, 104(6): 620–6).*
Adlakha et al. (Human Path, 25(2): 135–9.*
CA Plus—Frenette et al. (Can. J. Physiol. Pharmacol. 1985 63(12), 1603–7.*
Master*Tech Bulletin: Ultrum II Concentrate, American Master*Tech Scientific, Inc. P.O. Box 2539, Lodi, CA 95241–2539.
Frenette et al., *Can. J. Physiol. Pharmacol.* 63:1603–1607 (1985).

* cited by examiner

*Primary Examiner*—Jean C. Witz
(74) *Attorney, Agent, or Firm*—Marshall, Gerstein & Borun LLP

(57) ABSTRACT

The present invention relates to structures involved in the secretory processes of reproductive tissues, including the prostatic secretory processes, and their protein products which may have used as tools for diagnosing reproductive pathology including prostate disease. The present invention also relates to reagents, such as antibodies, other ligands and oligonucleotides, for detecting these structures o their contents and to methods of diagnosing prostate pathology, including prostate cancer and prostatitis. The invention further relates to an improved tissue and cell fixation process for the detection of secretory structures in reproductive tissue. The fixation process is useful for the diagnosis of prostate, testes and renal cancer.

17 Claims, 2 Drawing Sheets

X-ray diffraction analysis of sub-cellular and extra-cellular prostatic fractions EM x-ray diffraction analysis of cytoplasmic prostate secretory granules (PSG).

EM x-ray diffraction analysis of cytoplasmic regions between PSG.

EM x-ray diffraction analysis of luminal eosinophilic protein deposits (EPD).

EM x-ray diffraction analysis of corpora amylacea.

METHOD OF DIAGNOSIS OF PROSTATE CANCER

FIELD OF THE INVENTION

The present invention relates to structures involved in the secretory processes of reproductive tissues, including the prostatic secretory processes, and their protein products which may be used as tools for diagnosing reproductive pathology including prostate disease. The present invention also relates to reagents, such as antibodies, other ligands and oligonucleotides, for detecting these structures or their contents and to methods of diagnosing prostate pathology, including prostate cancer and prostatitis. The invention further relates to an improved tissue and cell fixation process for the detection of secretory structures in reproductive tissue. The fixation process is useful for the diagnosis of prostate, testes and renal cancer.

BACKGROUND OF THE INVENTION

The secretory (luminal) cells of normal prostatic glands are separated from the basement membrane by a layer of inconspicuous basal cells (1). This surface layer is characterised by its tall columnar cells with basally orientated nuclei, whose abundant apical cytoplasm synthesises a broad range of secretory proteases including prostate specific antigen (PSA) and prostatic acid phosphatase (PAP). Characteristically, the cytoplasm of surface secreting cells is optically clear to faintly eosinophilic which distinguishes it dramatically from the amphiphilic (dark) cytoplasmic staining of most dysplastic or malignant prostatic epithelial cells (2,3). Optimal tissue staining for diagnostic purposes yields maximal cytoplasmic clarity in benign prostatic secretory cells (2), the abrupt contrast between the cytoplasmic density of cancer and the pallor of the adjacent normal epithelium in well stained sections is often the most striking histologic feature which delineates the boundaries of a carcinoma focus. Conversely, a frequent problem in needle core diagnosis is the "clear cell" glandular atypical focus, in which confirmation of carcinoma is more difficult due to the absence of dark cytoplasm.

The significance of cytoplasmic density in adenocarcinoma is not understood. In the Gleason grading system (4) retention of clear cytoplasm implies a high level of differentiation since it is a requisite feature of all Grade 1 and Grade 2 carcinomas. Furthermore, cytoplasmic clarity is also characteristic of most adenocarcinomas which arise from the transition zone in association with nodular hyperplasia (5,6). Although dark cytoplasm is well described in dysplasia (PIN) and Gleason grade 3 carcinoma, it is not specific for malignant loss of differentiation since it is common in the cells of benign post inflammatory atrophy (7).

The organelles responsible for the appearance of the normal prostatic secretory cell cytoplasm have been described as myriad tiny vesicles which nearly fill the cytoplasm and appear completely devoid of content (1,8). These vesicles or granules are only faintly and variably recognisable by routine light microscopy, depending on the staining intensity of the faintly eosinophilic narrow septa which separate them.

Prostatic corpora amylacea (CA) are extracellular intraluminal structures seen in most adult prostate (9). The protein source of the CA is poorly understood although within these structures a group of sulphur-rich proteins have been previously detected (10). Similar sulphated proteins have also been detected in crystals associated with well-differentiated carcinoma, so-called prostatic crystalloids (11). Further, amyloid possibly related to β-2 microglobulin has been recognized in CA (12) but, despite these basic observations the origins of these extracellular prostatic structures is yet to be determined.

Round proteinaceous deposits have also been identified in prostatic luminae (9). These deposits (3–8 μm in diameter) are rare (8 cases of 166 specimens) and when noted are in close association with the luminal surface of the benign secretory cells confined to the central region of prostate in routinely fixed and processed tissues. The nature of this protein deposit is unknown but was noted to be negative for numerous protein fractions including, prostate specific antigen (PSA), prostatic acid phosphatase (PAP), light chain immunoglobulin (κ and λ), $\alpha_1$-antitrypsin and α-fetoprotein (9). Stains for mucin and silver stains were also negative but unexpectedly positive for phloxine tartrazine.

Beyond these initial observations, the detailed structure underlying the "clear cell" cytoplasmic appearance of prostatic epithelium as well as the relationships between this appearance and the process of prostatic exocrine secretion have never been systematically studied. Further, common and apparently fundamental alterations of structure and secretory function which must underly the abrupt transition to the dark cytoplasm of most cancers are unknown.

The mammalian oviduct provides an environment that supports the gametes, the process of fertilisation, early embryonic development and the delivery of a viable embryo to the uterus. The lumen of the mammalian oviduct is formed by a complex interdigitating system of longitudinal mucosal folds. These longitudinal mucosal folds are lined by a simple columnar epithelium and the morphological and biochemical characteristics of this epithelium are controlled by ovarian steroids. At the time of ovulation this lining epithelium consists of fully differentiated columnar ciliated and secretory cells. Approximately 40–50% of the epithelial cells are secretory. Secretory glands are observed in the apical regions of the cells. Several secretory products have been identified which enhance sperm motility, viability, binding to zona pellucida and enhance the rate of zona pellucida penetration. (Verhage et al 1997 Characteristics of an oviductal glycoprotein and its potential role in fertility control. J. Reproduction and Fertility Supplement 51:217–226).

SUMMARY OF THE INVENTION

The present inventors have now developed improved techniques for visualising prostatic cytoplasmic structure and the mechanism of cell secretion. These improved techniques have led to the surprising finding that secretory granules which are found in the luminal cells of normal prostate glands are absent in prostate carcinomas. These findings indicate that the prostate secretory granules may provide an important tool in the diagnosis of prostate cancers.

The present inventors have also identified a link between PSG, decapitated cytoplasmic body (DCB), eosinophilic bodies (EB) and corpora amylacea (CA) structures. Briefly, the normal secretory cell cytoplasm is filled with brightly eosinophilic PSG measuring about 1 μm in diameter and densely concentrated in the apical third of the cell. This apical compartment represents an apocrine secretory bleb. Periodic detachment of blebs carries packages of secretory granules (PSG) into the lumen where the receptacles fragment liberating their contents. The luminal cytoplasmic compartment (bleb), emptied of its protein enzymes, becomes a decapitated cytoplasmic body (DCB), a partly collapsed, faintly basophilic membrane with remnant cytoplasm. The DCB shrinks to form a sphere with a thickened, brightly eosinophilic surface casing, the eosinophilic body (EB). This structure may dissolve in luminal secretions, but it is also observed that it may adsorb to the surface of the corpus amylaceum (CA).

Unexpectedly, the present inventors have found that in prostatic adenocarcinomas, the entire secretory apparatus is substantially absent; neither PSG, DCB nor EB are found. An inability to form corpora amylacea arises from this fact. Prostate carcinomas may therefore be characterised by a significant reduction in levels, or absence, of any one of the structures associated with prostate secretions.

The present inventors have found that PSGs, EBs, DCBs and CAs may be readily visualised in normal prostate tissue which has been fixed in strong glutaraldehyde, or a substance which produces similar cytoplasmic fixation to that produced by strong glutaraldehyde.

Accordingly, in a first aspect the present invention provides a method of processing a tissue sample for analysis, the method comprising exposing the tissue sample to a composition which produces substantially identical cytoplasmic fixation to that produced by glutaraldehyde at a concentration of at least 2.0% and/or which provides substantially identical preservation of secretory granules as that provided by glutaraldehyde at a concentration of 2.0%.

In a preferred embodiment of the first aspect, the tissue sample is reproductive or renal tissue, more preferably reproductive tissue. Preferably, the reproductive tissue is prostatic, testes, fallopian tube or oviduct tissue.

In a further preferred embodiment, the histological analysis comprises analysing the tissue for the presence of secretory granules.

In a second aspect the present invention provides a method of diagnosing prostate pathology in a subject which method comprises (i) fixing a sample of prostate tissue from the subject in a fixative which produces substantially identical cytoplasmic fixation to that produced by glutaraldehyde at a concentration of at least 2.5%; and (ii) analysing the sample for the presence of PSG and/or EB and/or DCB and/or CA structures, or the contents of any one or more of these structures.

It will be appreciated that a reduced number of PSG and/or EB and/or DCB and/or CA structures, or the contents thereof, in the sample is indicative of prostate disease in the subject.

In a preferred embodiment, the method of the second aspect is used to diagnose prostatitis or prostate cancer in the subject.

In one embodiment of the second aspect, the analysis in step (ii) is performed by light microscopy. In this embodiment, the tissue is preferably stained with a stain such as haematoxylin and/or eosin.

In a further embodiment of the second aspect, the analysis in step (ii) involves electron microscopy.

In yet a further embodiment of the second aspect of the present invention, the analysis in step (ii) involves immunostaining. The immunostaining may involve immuno detection of PSA or PAP. Alternatively, the immunostaining may involve immuno detection of PSG and/or EB and/or DCB and/or CA structures.

In a further preferred embodiment of the first and second aspects, the fixative produces substantially identical cytoplasmic fixation to that produced by glutaraldehyde at a concentration of between 2.5% and 6%, more preferably at a concentration of between 3% and 5%. The fixative may comprise glutaraldehyde at a concentration of between 2.5% and 6%, more preferably at a concentration of between 3% and 5%.

In a further preferred embodiment of the first and second aspects, the fixative composition comprises an aqueous solution of glutaraldehyde at a concentration of between 2.5% and 6%, a metallic salt and a buffer stabiliser, the composition having a pH of between 5.7 and 5.75.

In a further preferred embodiment of the first and second aspects, the fixative further comprises phenol, preferably in a concentration ranges of from about 2.0 to about 3.0 g/l, more preferably around 2.5 g/l.

In a further preferred embodiment of the first and second aspects, the metallic salt is selected from the group consisting of zinc sulphate, copper sulphate, barium sulphate, cobalt chloride, barium chloride, potassium chloride, mercuric chloride and lead chloride. Preferably, the metallic salt is zinc sulphate.

In a further preferred embodiment of the first and second aspects, the concentration of the metallic salt ranges from 3.0 to 20.0 g/l, more preferably around 13.0 g/l.

In a further preferred embodiment of the first and second aspects, the buffer comprises one or more acetic acid compounds. Preferably, the buffer stabilizer comprises sodium acetate at a concentration of about 0.2M and acetic acid at a concentration of about 0.2M.

In a further preferred embodiment of the first and second aspects, the fixative further comprises one or more components selected from the group consisting of:

Detergents such as SDS, Tween (0.001%–1.0%),

Azone (laurocaprame 1-dodecylazacyclo-hepton-2-one) 3% w/v or 1-geranylazacyclohepton-2-one 3% w/v, Liposomes, Sodium taurocholate 40–0.25 $\mu$M; (which may include:
 Cholesterol 0.2 mM–0.075mM
 Oleicacid 1 mM–0.25mM
 Synthetic phospholipids, eg phosphocholin 14–18 10–30 mM as mixed micells), Solution C24 (polyoxyethene-24-cholesterol-ether), Polyethylene glycol 200 dilaurate (0.1–10%), Menthol 1% w/v, Mercaptoethanol (0.0025%), Glycerol trioleate, Terpene penetration enhancers (for example 1,8-cineole, methane, (+)-limonene, nerolidol), Medium chain fatty acids (caproate C6, C8 caprylate, C10 caprate, C12 laurate), Trichloroactic acid (0.5–5.0%), Metallic salts (for example, zinc sulphate, potassium chloride, calcium chloride, zinc chloride) (3–30%), Dimethylsulfoxide (0.1–20%), Mono and disaccharides (glucose), Urea, and Methyl salicylate.

In a third aspect the present invention provides a histological fixative composition comprising an aqueous solution of glutaraldehyde, a metallic salt and a buffer stabiliser, the composition having a pH of between 5.7 and 5.75.

In a preferred embodiment of the third aspect, the amount of glutaraldehyde ranges from about 2.5% and about 6%, more preferably between about 3.5% and about 5%, by volume of the composition.

In a further preferred embodiment of the third aspect, the fixative comprises phenol, preferably in a concentration ranges of from about 2.0 to about 3.0 g/l, more preferably around 2.5 g/l.

In a further preferred embodiment of the third aspect, the metallic salt is selected from the group consisting of zinc sulphate, copper sulphate, barium sulphate, cobalt chloride, barium chloride, potassium chloride, mercuric chloride and lead chloride. Preferably, the metallic salt is zinc sulphate.

In a further preferred embodiment of the third aspect, the concentration of the metallic salt ranges from 3.0 to 20.0 g/l, more preferably around 13.0 g/l.

In a further preferred embodiment of the third aspect, the buffer comprises one or more acetic acid compounds. Preferably, the buffer stabilizer comprises sodium acetate at a concentration of about 0.2M and acetic acid at a concentration of about 0.2M.

In a further preferred embodiment of the third aspect, the fixative composition further comprises one or more components selected from the group consisting of:

Detergents such as SDS, Tween (0.0.01%–1.0%),

Azone (laurocaprame 1-dodecylazacyclo-hepton-2-one) 3% w/v or 1-geranylazacyclohepton-2-one 3% w/v, Liposomes, Sodium taurocholate 40–0.25 $\mu$M; (which may include:
  Cholesterol 0.2 mM–0.075mM
  Oleicacid 1 mM–0.25mM
  Synthetic phospholipids, eg phosphocholin 14–18 10–30 mM as mixed micelles), Solution C24 (polyoxyethene-24-cholesterol-ether), Polyethylene glycol 200 dilaurate (0.1–10%), Menthol 1% w/v, Mercaptoethanol (0.0025%), Glycerol trioleate, Terpene penetration enhancers (for example 1,8-cineole, methane, (+)-limonene, nerolidol), Medium chain fatty acids (caproate C6, C8 caprylate, C10 caprate, C12 laurate), Trichloroactic acid (0.5–5.0%), Metallic salts (for example, zinc sulphate, potassium chloride, cobalt chloride, calcium chloride, zinc chloride) (1–30%), Dimethylsulfoxide (0.1–20%), Mono and disaccharides (glucose), Urea, and Methyl salicylate.

In a particularly preferred embodiment the fixative is prepared as follows:
(i) Phenol (2.5 g) is dissolved in 50 ml of distilled water. The phenol solution is added to 200 ml of glutaraldehyde (25%). The pH of the solution is adjusted to 5.8 by the dropwise addition of 5M NaOH.
(ii) Zinc sulphate (15 g) is dissolved in 250 ml of distilled water. The zinc sulphate solution is then admixed with 470 ml of 0.2 M sodium acetate and 30 ml of 0.2 M acetic acid. The solution is adjusted to a pH of 5.6–5.75.
(iii) The solutions from steps (i) and (ii) are admixed and if necessary, the pH and is adjusted by the addition of NaOH to about 5.7.

Preferably, the final solution is filtered before use.

In a fourth aspect the present invention provides an isolated prostate secretory granule (PSG).

By "prostate secretory granule" or "PSG" we mean a vesicle which is produced in and secreted from normal prostatic secretory cells.

In a preferred embodiment the PSG has a diameter of 800–1200 nm. In a further preferred embodiment, the PSG has a granular electron dense core without internal membranes.

In a further preferred embodiment, the PSG is eosinophilic.

In a further preferred embodiment, the PSG is glycoprotein and sulphur rich.

In a fifth aspect the present invention provides an isolated prostate cell decapitated cytoplasmic body (DCB).

In a further preferred embodiment, the DCB is glycoprotein and sulphur rich.

In a sixth aspect the present invention provides an isolated prostate eosinophilic body (EB).

In a preferred embodiment, the EB is glycoprotein and sulphur rich.

In a further preferred embodiment, the EB has a diameter of between 4 and 15 $\mu$m.

In a seventh aspect the present invention provides an isolated prostate corpora amylacea (CA).

In a preferred embodiment, the CA is glycoprotein and sulphur rich.

The present inventors have found that the contents of the PSG and/or DCB and/or EB and/or CA include sulphur-rich prostatic crystalloids, extracellular acid mucin and sulphate-associated glycosaminoglycans. The sulphate-associated glycosaminoglycans may be rich in glucosamine and galactose. The present inventors have also characterised the sulphated-associated compounds and have identified the substance keratan sulphate as the major sulphur group of PSG, DCB, EB and CA structures.

Accordingly, in an eighth aspect the present invention provides an isolated keratan sulphate-associated compound derived from a PSG and/or DCB and/or EB and/or CA.

One particular keratan sulphate-associated compound has been purified and characterised by molecular weight analysis.

Accordingly, in a ninth aspect the present invention provides a keratan sulphate-associated compound derived from a PSG, the compound having a molecular weight of about 70–75 kDa.

It will be appreciated by those skilled in the art that a PSG and/or DCB and/or EB and/or CA structures or the contents of these structures may be used to generate binding ligands, such as antibodies against a PSG and/or DCB and/or EB and/or CA or the contents thereof. These binding ligands may be used in turn as diagnostic tools in the differentiation of normal and malignant prostate tissue, in situ or by their presence in bodily fluids.

Accordingly, in a tenth aspect the present invention provides a binding ligand, preferably an antibody, directed against a PSG and/or DCB and/or EB and/or CA or the contents thereof.

The term "antibody" is to be construed as covering any specific binding substance having a binding domain with the required specificity for the secretory structure. Thus, the term covers antibody fragments, derivatives, functional equivalents and homologues of antibodies, including any polypeptide including an immunoglobulin binding domain, whether natural or synthetic. Chimaeric molecules including an immunoglobulin binding domain, or equivalent, fused to another polypeptide are therefore included.

It is also possible that the PSG and/or EB and/or DCB and/or CA structures include nucleic acid molecules. In this case, as would be readily understood by those skilled in the art, the presence of these structures or their contents in tissue could be detected using oligonucleotide probes. The oligonucleotides could also be used in the amplification of the nucleic acid contents, for example, by PCR. The present invention also provides such oligonucleotides.

In an eleventh aspect the present invention provides a method of analysing tissue for pathology, the method comprising detecting the presence of secretory granules in a sample of the tissue.

In a preferred embodiment of the eleventh aspect, the tissue sample is reproductive tissue. Preferably, the reproductive tissue is prostatic, testes, fallopian tube or oviduct tissue. More preferably, the tissue is prostatic tissue.

In a further preferred embodiment of the eleventh aspect the pathology is prostate cancer or prostatitis.

In a further preferred embodiment of the eleventh aspect the analysis involves fixing the tissue sample with a composition according to the third aspect.

In a twelfth aspect the present invention provides a method of diagnosing prostate pathology in a subject which method comprises analysing a fluid sample from the subject for the contents of PSG and/or EB and/or DCB and/or CA structures, or the contents thereof. It will be appreciated that a decrease in any one of the structures of the contents thereof (when compared to a fluid sample from a subject without prostate disease) in the fluid sample is indicative of prostate disease. The body fluid may be blood, serum, semen or urine.

In a preferred embodiment of the twelfth aspect, the disease is prostate cancer or prostatitis.

In a further preferred embodiment of the twelfth aspect the analysis involves immunoanalysis using a binding ligand, preferably an antibody, according to the tenth aspect of the present invention.

In a further preferred embodiment of the twelfth aspect, the contents of any one or more of the structures comprises a sulphate-associated compound according to the eighth or ninth aspects.

In a thirteenth aspect, the present invention provides a method of monitoring the effectiveness of the use an anticancer agent in the treatment of prostate cancer in a subject which method comprises obtaining sequential samples of fluid from the subject over a period of time of treatment and detecting the levels of PSG and/or EB and/or DCB and/or CA structures, or the contents thereof, in the sequential samples.

In a preferred embodiment of the thirteenth aspect of the present invention, the fluid sample is derived from blood serum, seminal fluid, or urine.

It is known that a number of anticancer agents act by inhibiting the assembly of microtubules in tumour cells (13). It now also appears that inhibition of microtubule assembly disturbs secretion of granules, such as prolactin granules, from secretory glands (14). Accordingly, anticancer agents may inhibit the secretion of PSGs from prostate tumour cells.

Accordingly, in a fourteenth aspect the present invention provides a method of screening an agent for anticancer activity, which method comprises
(i) exposing a sample of prostate tumour cells to the agent, and
(ii) monitoring the cells over time for the presence of PSG and/or EB and/or DCB and/or CA structures, wherein the presence of one or more of the structures in the cells indicates that the agent has anticancer activity or allows maturation of cancer cells, thereby making them susceptible to other agents.

In a preferred embodiment, the prostate tumour cells are cultured cells. In a further preferred embodiment, the cultured cells are obtained by transformation of normal prostate luminal cells.

In a fifteenth aspect the present invention provides a method of screening an agent for anticancer activity, which method comprises
(i) exposing a sample of prostate cells to a transforming substance, wherein the level of exposure is sufficient to transform the prostate cells into prostate tumour cells,
(ii) exposing the cells to the agent and
(ii) monitoring the cells over a period of time for the presence of PSG and/or EB and/or DCB and/or CA structures, wherein the maintenance of one or more of the structures in the cells over the period of time, or an increase in the level of one or more of the structures over the period of time, indicates that the agent has anticancer activity.

The prostate cells may be exposed to the agent simultaneously with the transforming substance, or subsequent to exposure to the transforming substance.

The transforming substance may be any substance which transforms normal cells to tumour cells. Examples of suitable transforming substances comprise the Epstein Barr Virus.

In a further preferred embodiment, the cells are monitored for a period of 7 days, more preferably 28 days.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

DETAILED DESCRIPTION OF THE INVENTION

Figure 1:
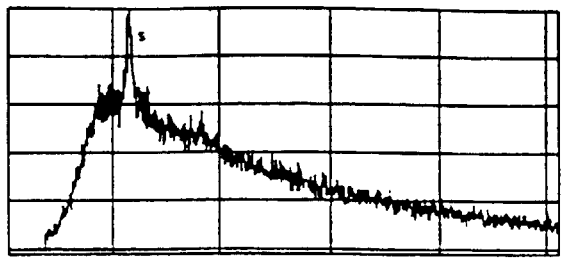
FIG. 1 X-ray diffraction analysis of sub-cellular and extra-cellular prostatic fractions.
Figure 1:
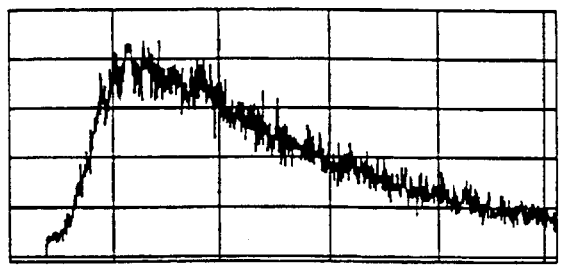
Figure 1:
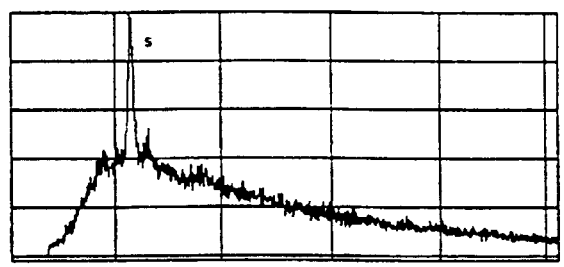
Figure 1:
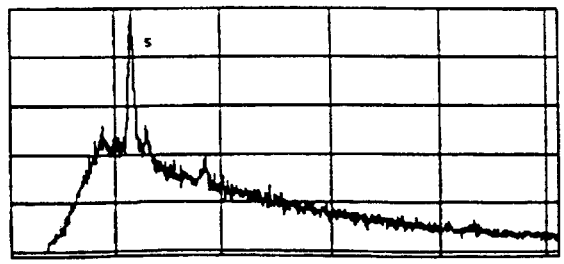

In order that the nature of the present invention may be more clearly understood preferred forms thereof will now be described with reference to the following Examples.

EXAMPLE 1

Identification of Prostate Sectretory Granules (PSGs)

Materials and Methods

Twenty four radical prostatectomy specimens were received fresh either in the Auckland Hospital laboratory [19 cases] or at Stanford University laboratory [5 cases]. The prostates were orientated vertically, a probe inserted through the urethra and a transverse section cut through the lobe thought to harbour the main tumour mass. Hyperplastic tissue from the transition zone (TZ) as well as tumour and benign tissue from the periphery was sampled. In three cases, two with coexistent peripheral zone (PZ) carcinomas, well-circumscribed bright yellow TZ tumours were recognised and were sampled separately. Tissue samples from each area were fixed in the following solutions; 95% ethyl alcohol, 4% and 10% buffered formaldehyde, 1%, 3%, and 5% buffered glutaraldehyde, 6% mercuric chloride in 1% formaldehyde (B5), and picric and acetic acid in 10% formaldehyde (Bouin's solution). After 12–18 hours all fixed tissues were processed through graded alcohols to paraffin wax. In further descriptions buffered glutaraldehyde in concentrations greater than 2.5% is referred to as "strong glutaraldehyde".

Three micron sections were cut and stained with routine haematoxylin and eosin (H&E), anti-prostate specific antigen (PSA; Dako Corp, Denmark, 1:100), anti-prostatic acid phosphatase (PAP; Dako Corp, Denmark, 1:100) and cytokeratin AE1/AE3 (Dako Corp, Denmark, 1:100). In the three cases of TZ cancer, samples from the tumours and adjacent benign prostatic tissues were snap frozen in cold hexane (−78° C.) and 4 micron sections were stained for lipids using Sudan IV and Sudan black B stains.

For electron microscopy, one mm tissue fragments from tumour and benign tissues of six cases including the three TZ cancers, were fixed in either 3% buffered glutaraldehyde or 4% buffered formaldehyde. Tissues were post fixed in 1% osmium tetroxide, dehydrated through graded alcohols and embedded in epoxy resin. Ultra-thin sections (90 nm) were cut, then stained with uranyl acetate and lead citrate and viewed in a transmission electron microscopy at 100 kv.

Ultrastructural immunostaining for PSA was performed on benign and malignant tissues from two of the six cases examined by electron microscopy. Samples were fixed in strong glutaraldehyde for 12 hours and following sucrose impregnation, frozen thin and semi-thin sections were cut on a vibrating ultramicrotome. Antigen recognition was demonstrated with strepavidin/gold (Zymed Inc. 1:10).

PSGs may be isolated from fresh prostate tissue which is teased through a stainless steel mesh to separate the epithelial cells and their contents from the stroma. Cells and cytoplasmic fragments can then be collected in a buffered sucrose solution which is then subjected to ultracentrifugation. This method will provide a pure isolate of granules. Similarly, DCPs, EBs and CAs may be isolated at lower speed centrifugation. Electron microscopy will confirm correct isolation speeds.

Results

Light Microscopy

In all cases, benign prostatic secretory cells fixed in ethyl alcohol, 4% and 10% formaldehyde, 1% glutaraldehyde, mercuric chloride and Bouin's solution showed abundant clear or palely eosinophilic cytoplasm. In contrast, benign surface cells fixed in strong glutaraldehyde solutions contained brightly eosinophilic cytoplasmic prostatic secretory granules (PSG) which, although sometimes concentrated towards the luminal surface of the cell frequently filled the entire cell cytoplasm. The contrast between eosinophilic granule staining and background was greatly intensified by thorough washing of the H&E sections in running tap water for 45 minutes which removed all traces of eosin bar that staining the granules. In the strong glutaraldehyde fixed tissue, many secretory cells showed apical cytoplasmic buds and others were associated with cytoplasmic decapitations, both structures filled with eosinophilic PSG. Although identifiable in alcohol, formaldehyde or mercuric chloride fixed tissue these projections were less easily visualised due to their marked pallor and inconsistent membrane staining.

In areas of high grade dysplasia PSG were markedly reduced in number (90%+) or absent. Also no granules were seen in 17 of 22 peripheral zone Gleason grade 3 and 4 invasive cancer samples. Four of the remaining five samples showed only isolated clusters of a few PSG in the apical regions of individual cells. There remained a single Grade 3 cancer sample in which the cells contained frequent cytoplasmic PSG; about half the density seen in benign cells. An adjacent formaldehyde fixed tissue sample in this isolated case showed it to have clear cell morphology.

The remaining PZ cancers and all dysplasias after either formaldehyde or glutaraldehyde fixation showed uniformly dark (amphiphilic) cytoplasm, but in contrast to formaldehyde, strong glutaraldehyde fixed benign glands adjacent to tumour cells contained red PSG.

Clear cell TZ carcinoma showed no granular cytoplasmic material. One case of this total series an area classified as atypical adenomatous hyperplasia (adenosis) was recognised and despite an infiltrating architectural pattern, cytoplasmic granules were evident in reduced numbers (30–40% of those seen in benign glands) throughout the cell cytoplasm, suggesting a diagnosis of benign atypia.

Fat stains on frozen sections confirmed that the cytoplasm of most cells in clear cell TZ carcinoma were filled with numerous supranuclear lipid vacuoles. In contrast, benign cells contained almost no lipid except for an occasional lipid droplet consistently located below the nucleus and adjacent to the basal cell layer. In clear cell cancers processed routinely after formaldehyde fixation, abundant supranuclear fat droplets produced an appearance almost identical to that of benign "clear" cells. In contrast after strong glutaraldehyde fixation, the persistent clear cytoplasm of the cancer provided histologic delineation of the tumour focus by its boundary of benign red granular cells.

Immunostains

After strong glutaraldehyde fixation, cytoplasmic granules in benign epithelium showed sharply delineated immunoreactivity for both PSA and PAP with approximately 50% of all granules staining intensely for these markers. The immunoreactivity within granules was discrete and intense in contrast to negative or weakly stained background cytoplasm. Some secretions within the lumen also retained a finely granular immunoreactivity. Counterstaining with eosin confirmed that all apical granules were immunostained while basal and mid zone granules were usually negative. In contrast the cytoplasm of the benign secretory cells fixed in formaldehyde, alcohol, mercuric chloride and Bouin's stained diffusely for these prostate markers without any evidence of granularity.

With few exceptions, carcinoma cells fixed in strong glutaraldehyde showed no granular staining for either PSA or PAP.

Electron Microscopy The prostatic secretory granules (PSG) identified by light microscopy in the tissue fixed in strong glutaraldehyde were membrane bound organelles 900–1000 nm in diameter and contained a electron dense granular material. No internal membrane structures were observed. These granules were identified basally in small numbers adjacent to the nucleus in close proximity to Golgi and rough endoplasmic reticulum and nearly filled the cytoplasm more apically.

In many cells the apical cytoplasm was partly separated from the rest of the cell by inward extension of the apical cell membrane; these cytoplasmic luminal projections containing many granules often merged with the luminal prostatic secretions. This was seen even in cells where the cytoplasmic bud had not yet separated from the underlying cell. Electron microscopic examination of formaldehyde fixed normal secretory cells tissue showed fragmented and collapsed membrane bound structures in an identical distribution to those granules seen in strong glutaraldehyde fixed tissue.

In strong glutaraldehyde fixed tissue, immunogold deposition indicated localisation of PSA and PAP specifically to many of the apical granules of benign secretory cells without marking the intervening cytoplasm. Cancer cells fixed in strong glutaraldehyde did not contain any granules, instead an increased concentration of ribosomes and endoplasmic reticulum was seen throughout the cytoplasm. Immunogold staining recognised PSA in the cytoplasm particularly near the cell membrane.

Discussion

The distinctive cytoplasmic clarity of normal prostatic secretory epithelium is revealed by our data to be the manifestation of a fixation artefact. Formaldehyde and a number of alternate routine fixatives damage the epithelial cells, disrupting their apparently fragile secretory granules that lose their contents. We are able to prevent this damage by prompt fixation in strong glutaraldehyde, which preserves the intact secretory granules (PSG) and reveals their brightly eosinophilic contents. Distinctively, the granules retained full intensity of stain after tap water washing for a period far longer than needed to remove all other traces of eosin from the slide. This unusual selective staining persistence is also known to characterise other acid phosphatase secreting protease granules such as those of the eosinophil leucocyte (15,16). Hence, we propose that both cationic proteins and structural phospholipids of the secretory granules should be further investigated as likely determinants of this unusual behaviour.

Ultrastructurally, prostatic secretory granules (PSG) were about 1000 nm in diameter, a dimension consistent with their visualisation by light nicroscopy. They contained a granular electron dense core without internal membranes or structure. With both light and electron microscopy PSA and PAP were localised exclusively to the contents of intact secretory granules. This observation depends upon fixation in strong glutaraldehyde and therefore this report represents the first definitive localisation of these important exocrine products.

The PSG which we describe were the only secretory organelles identified in this Example. In a previous study very occasional, still larger eosinophilic masses were identified in the cytoplasm of some large transition zone ducts (9). These ductal structures were negative for PSA and PAP and are presumed to be degenerate PSG or accumulations of their structural components; they were not seen in any tissue samples from this current series.

Although prostatic secretory granules have not been previously described in detail, ultrastructural observations of seminal plasma have reported variably sized membrane bound secretory structures called "prostasomes" measuring 20–250 nm in diameter and identified ultrastructurally in seminal plasma (17,18) and often partitioned into clusters. They were believed to be secreted from the cell by a process of exocytosis or diacytosis. By contrast, the PSG identified in this paper were 1000 nm in diameter, showed no internal subdivision, and displayed an apocrine secretion without evidence of exocytosis or diacytosis. There does not appear to be a direct relationship between the intracytoplasmic structures seen in this study visible by light microscopy and those minute prostasomes previously identified ultrastructurally in the seminal plasma.

Some features of normal prostatic granule formation and maturation were also visualised in our sections. Basally near the Golgi apparatus, granules were sparse and stained with eosin alone (negative for PSA and PAP). With increasing distance from the cell base, protease immunostaining became more intense along with increasing PSG density. This is consistent with the initial production of a pre-PSA molecule, which acquires biochemically activity and antigenicity with proximity to the cell apex.

The secretory process for the PSG has been described in broad outline and was confirmed here in detail. The area where PSG were most closely spaced and intensely stained was the apical third of the secretory cell cytoplasm. This apocrine secretory compartment was further immunohistochemically delineated by an abrupt absence of cytokeratin staining, indicating a loss of apical cytoplasmic filaments. The resultant fragile apical sac was observed to regularly disintegrate in-situ at the cell surface without detaching and its contents merged with the luminal secretion as individual PSG. These apical details were lost with formaldehyde fixation, but even with routine preparations the ragged, uneven and focally indistinct luminal cell border of the epithelium identified the distinctive features of the normal prostatic cell secretory process.

By contrast, in dysplasia (PIN) and in moderately well differentiated carcinomas with dark (amphiphilic) cytoplasm (Gleason 3), there were dramatic deviations from the normal secretory cell structure. Except for sparsely scattered PSG in a few cells, dysplasia and cancer alike showed no evidence of granule synthesis. Immunostainable PSA and PAP were variably demonstrated in cancer, but were released free into the cytoplasm and tended to be more sharply localised along the surface cell membrane. Further investigation of this drastic alteration in cell function within adenocarcinoma cells might help to explain phenomena such as epitope differences in cancer-produced PSA (19) as well as the greater affinity of PSA in cancer for alpha-1-antichymotrypsin (20).

In clear cell carcinomas of the transition zone, retention of normal PSG production was expected from observations on formaldehyde fixed tissue. But surprisingly granule production suffered the same fate of obliteration seen in dark cell carcinomas and dysplasias. Cytoplasmic clarity here depended on an alternate and aberrant pathway of differentiation in which the secretory product was lipid contained in tiny secretory droplets. On this basis transition zone clear cell carcinomas can now be definitively classified as a biologically distinct entity by their commitment to functions which have no parallel in the normal prostate nor in carcinomas with dark cytoplasm.

Clear cell areas of peripheral zone cancers in this series showed the same cytoplasmic features as those in the transition zone. There was a single exception (4% of cases) in which a peripheral zone clear cell carcinoma area continued to produce abundant normal PSG. In all other clear cell cancers, the depletion of PSG and concurrent establishment of a lipid synthesis pathway would suggest the culmination of a complex sequence of epigenetic changes whose early stages might well predate the emergence of invasive carcinoma. Nothing is yet known about possible premalignant alterations in clear cell carcinoma since special fixation is needed to reveal this pathway.

If strong glutaraldehyde is used in routine fixation, clear cell carcinomas will persist as foci with clear cytoplasm sharply outlined by a border of benign glands with intensely red granular cytoplasm. A commercial fixative Ultrim II (American Histology Reagent Company Lodi Calif.) may used rather than glutaraldehyde because it produces the same cytoplasmic fixation, is less toxic and preserves finer nuclear detail. This method of fixation will provide a practical manner in future studies to more reliably distinguish clear cell malignancies, to evaluate premalignant phases of clear cell cancer and to better characterise atypical glandular proliferations now classified as adenosis or atypical glandular hyperplasia (21,22) whose biological status remains obscure at this time. Further, this method can enhance the evaluation of prostatic tissue on a gland by gland basis in small samples such as needle biopsies.

EXAMPLE 2

Identification of Eosinophilic Protein Deposit (EPD)

Materials and Methods

Hyperplastic prostatic tissue (4 cases) as well as tumour and benign tissue from the periphery of the gland (2 cases) were collected as described in Example 1. Tissues from each area were divided into half; one half then fixed in 3% buffered glutaraldehyde, the other in 4% buffered formaldehyde. After 12–18 hours, fixed tissues were divided into 4 mm cubes and then dehydrated through a process of freeze-drying; the fixed tissue was immersed in liquid butane (−200° C.) then dehydrated under vacuum conditions for 48 hours. Finally, the specimens were gradually warmed to +58° C. in the vacuum and immersed in liquid wax. Control tissue processed routinely from adjacent areas was available in each case. The micron sections were cut and stained with routine H&E, alcian blue (pH 2.5), Congo red, phloxine tarterazine, anti-prostate specific antigen (PSA; Dako Corp, Denmark, 1:100) and anti-prostatic acid phosphatase (PAP; Dako Corp, Denmark, 1:100) and $\beta$-2 microglobulin Dako Corp, Denmark, 1:100). In an attempt to identify chemical differences between the different eosinophilic structures, test and control samples were subjected to X-ray diffraction studies. Three micron sections were cut on onto melinex film, electrostatically coated with carbon film. Thereafter, the sections were examined with a black-scatter detected in a scanning electron microscope (PSEM 500) at 25 KV and a spot size of 0.25 microns. Specific protein deposits i.e. CA and crystalloids as well as PSG were targeted and analyzed using an EDAX detection unit (P500 EDS) for 100 seconds.

Results

In all benign tissue the prostatic luminae were filled with round intensely eosinophilic proteinaceous deposits (EPD) measuring 4–15 $\mu$ in diameter. These were most numerous in lumen of larger ducts and were often seen surrounding and merging with prostatic corpora amylacea. These structures were in contrast to PSG were negative on immunostaining for PSA and PAP. Stains for alcian blue confirmed weak staining of PSG but intense staining of EPD. The alcian blue staining of the EPD was concentrated in a beaded corona surrounding a pale protein core. All tumours and control formaldehyde fixed benign tissue showed no associated PSG or intraluminal EPD.

X-ray diffraction studies showed abundant sulphur-rich material in both PSG and EPD (FIG. 1) in freeze dried material fixed in glutaraldehyde.

Discussion

PSG is a complex protein constituent of benign secretory cells which is now recognized to be intimately associated with a previously uncharacterized alcohol-soluble eosinophilic protein deposit (EPD). The failure to previously recognize EPD (9) is based on their alcohol solubility. Analyses performed in prostate tissue protected from alcohol elution (current freeze drying techniques) confirms that most glands contain abundant EPD. The deposits of EPD fill the ducts of the gland and in turn surround and merge with intraluminal corpora amylacea.

EPD consists of a protein core, which is intensely eosinophilic and like PSG, is resistant to tap water washing. Its outer rim is composed of a glycoprotein rich, alcian blue positive material which also stains more intensely with phloxine tartrazine. Phloxine tartrazine identifies viral inclusions although keratin and granules of intestinal paneth cells are also strongly stained.

Prostatic crystalloids, a common feature of well-differentiated carcinoma, share some of the staining characteristics of EPD in that they are intensely eosinophilic and resistant to water elusion. In contrast to EPD they lack a glycoprotein component, the absence of which may relate to an alternate secretory mechanism of glycoproteins by cancer cells and the subsequent presence of abundant extracellular acidic mucin.

EXAMPLE 3

Prostate Secretory Apparatus: PSG, DCP, EB and CA Structures

Materials and Methods

Prostatic tissue with nodular hyperplasia (5 cases), together with benign and carcinoma tissue from the peripheral zone of the prostate (6 cases) were collected from eight radical prostatectomy specimens received in this laboratory. Tissues from each area were divided into three portions; one fixed in 3% buffered glutaraldehyde ("Solufix"®), the second in 4% buffered formaldehyde and the third kept unfixed on ice. After 12–18 hours, fixed tissues were divided into 4 mm cubes and were processed in three separate ways; (i) routinely to wax paraffin through standard alcohol dehydration, (ii) through propylene oxide to epoxy resin and (iii) to paraffin wax by dehydration through a process of freeze-drying. This latter method relied on the fixed tissue being immersed in liquid propane (−120° C.), dehydrated under vacuum conditions for 18 hours and then warmed to +58° C. and immersed in liquid wax. In addition to material taken from fresh radical prostatectomy specimens, archival material from prior samples taken at radical prostatectomy were also examined. These samples consisted of three peripheral zone cancers as well as three transitional zone carcinomas rich in prostatic crystalloids. Samples from these six cases were bisected at the time of surgery and half was fixed in 3% glutaraldehyde the other half in 4% formaldehyde. All six cases were processed routinely through alcohol and embedded in wax.

The unfixed prostate samples (benign and malignant) were homogenized and centrifuged through a 0.25M sucrose solution. Pellets and supernatant were collected after centrifugation at 15,000 g, 18,000 g and 20,000 g. All pellets were divided for electron microscopy and routine polyacrylamide gel electrophoresis. Further, prostatic concretions were extracted from benign tissue and purified through multiple washings in saline solution. Light microscopy was used to confirm successful extraction and polyacrylamide gel electrophoresis was performed. Samples of PSG and concretions were submitted to high performance exchange chromatography (Dionex DX 500 carbohydrate system) to assess carbohydrate and amino acid content. Washed concretions were also subjected to X-ray analysis using a Rigaku RU-300 rotating anode X-ray generator producing Cu $K_\alpha$ radiation of wavelength 0.154 nm with focusing optics. Diffraction patters, which are dependent on the presence of true crystals, were recorded for 20 minutes by a "Mar-Research 345" image plate area detector.

Routinely processed glutaraldehyde and formalin fixed tissues as well as freeze dried and plastic embedded material were cut (plastic embedded tissue at 1 µm and paraffin embedded tissue at 3 µm) and stained with routine haematoxylin and eosin (H&E) as well as histochemical and immunostains. These included periodic acid Schiffs (PAS), alcian blue (pH 2.5, pH 1.0), Congo red, phioxine tartrazine, anti-prostate specific antigen (PSA; Dako Corp, Denmark, 1:100), anti-prostatic acid phosphatase (PAP; Dako Corp, Denmark, 1:100), β-2 microglobulin (Dako Corp, Denmark, 1:100), and sialosyl-Tn antigen (STn; Dako 1:50). Heat antigen retrieval was used for β-2 microglobulin as recommended in the product brochure.

X-ray diffraction was performed with the aid of scanning electron microscopy; two selected formalin fixed samples, three glutaraldehyde fixed samples as well as two freeze dried glutaraldehyde-fixed tissue samples were assessed targeting the PSG, concretions, crystalloids and other eosinophilic structures. Three-micron sections were cut onto melinex film and electrostatically coated with carbon. Thereafter, the sections were examined with a back-scatter detector in a scanning electron microscope (PSEM 500) at 25 kV and a spot size of 0.25 µm. Results were analyzed using an EDAX detection unit (P500 EDS) for 100 seconds. Control areas in the gland lumen, cytoplasm (between PSG) and surrounding stroma were also targeted.

Results

Histology

In all benign tissues fixed in glutaraldehyde, numerous bright red PSG were visualised in the surface secretory cells and showed concentration in the apical portion of the cell cytoplasm. These apical apocrine compartments (blebs) of different cells were in various stages of formation and shedding, giving an uneven surface border. After detaching from the luminal surface of the secretory cell, the evolving blebs changed from tear drop shape to a spherical contour and after losing their eosinophilic contents (PSG) they became pale blue membrane ghosts which filled the gland lumens and which we called "decapitated cytoplasmic bodies" (DCB). The DCB were 8–15 µm in diameter and centrally they merged with the prostatic secretions and became indistinct (Table 1). None of these observations could be made on formalin-fixed tissue which had empty appearing cell cytoplasm and gland lumens.

In tissues processed by freeze drying and stained routinely with haematoxylin and eosin, many DCB acquired a discrete brightly eosinophilic rim, contrasting with a central darker red core. As a result many of these DCB could be distinguished from central prostatic secretions and we termed these eosinophilic bodies (EB). Centrally, they were most numerous often overlapping and ranging in size from 4–8 µm. In lumens of larger ducts EB could be seen fusing with the surface of existing corpora amylacea, adding in a lamellar fashion to the corpora diameter, or forming small intraluminal concretions. None of the above findings could be visualized in formalin-fixed tissue.

Among prostatic adenocarcinomas, Gleason grade 3 with amphiphilic cytoplasm and architecturally simple gland structures comprises the most common histological acinar pattern. After glutaraldehyde fixation and either plastic embedding or freeze drying, the cytoplasm in nearly all such malignant cells was almost completely devoid of the PSG which fill benign cell cytoplasm. PSA and PAP were accordingly displaced from their normal location and were diffuse in the cytoplasm with strong accentuation at the apical plasma membrane. Luminal DCB and EB were almost never seen (Table 1).

Clear cell carcinoma is the commonest histologic pattern for transition zone carcinomas, but, in the present series, it appeared mainly in peripheral zone as islands of cancer with clear cytoplasm and Gleason grade of 3 or less. The line of transition to surrounding amphiphilic grade 3 cancer was usually sharp. Near this border on the amphiphilic side, the dark tumour cells were often accompanied by intraluminal mucin; within the clear cell cancer nidus, mucin was almost always absent, and occasional groups of lumens contained dense, brightly eosinophilic crystalloids. Many of these cancer lumens also contained a granular pale eosinophilic protein matrix that surrounded the crystalloids (12) and was most easily recognized in glutaraldehyde fixed tissues. The cytoplasm of most clear cells had few or no PSG, but gland lumens containing crystalloids were surrounded by epithelium having a higher concentration of PSG but never approaching that of benign epithelium.

TABLE 1

Frequency of Prostate Associated Intra- and Extracellular Protein Structures in benign, dysplastic and neoplastic tissues.

|  | Benign | Dysplasia | Carcinoma |
|---|---|---|---|
| Prostate Secretory Granules (PSG) | +++ | ± | ± |
| Decapitated Cytoplasmic Bodies (DCB) | +++ | ± | − |
| Eosinophilic Bodies (EB) | ++ | − | − |
| Corpora Amylacea (CA) | + | − | − |
| Crystalloids | − | − | ± |

Frequency: 75–100% (+++), 50–75% (++), 10–50% (+), 1–10% (±) and 0% (−)

Analysis of Luminal Contents vs Cell Cytoplasm

PSG contained 20% sugar by weight. This comprised 1.76 nmol/µl of glucosamine, and 0.64 nmol/µl of galactose and 0.4 nmol of galactosamine (total of 2.8 nmol/µl). Proteins were estimated at 0.1 nmol/µl and thus the molar ratio of monosaccharides/amino acids was 30:1. Amino acid analysis did no show significant concentrations of sulphur containing fractions (<3%) and the most common amino acids identified were glycine (8.9%), proline (8.9%), leucine (8.8%) alanine (7.9%), and valine (7.9%). Equimolar concentration of sulphate to glucosamine was identified confirming the components of sulphated glycosaminoglycans of proteoglycans.

Analysis of the corpora amylacea also confirmed a large concentration of glucosamine (1.2 nM/µl) and galactose (0.86 nM/µl) in relation to protein (1.0 nM/µl). Amino acid analysis confirmed significant concentrations of alanine, valine and proline and as in the PSG sulphur-containing amino acids represented a minority of the total amino acids (<3%). An equimolar concentration of sulphate (1.1 nM/µl) to glucosamine was also detected. Monosaccharide/amino acid ratio of corpora amylacea was 2:1.

X-ray crystallography of the corpora amylacea demonstrated wide dispersion patterns consistent with a true biological crystal composed of very small sub-units (less than 200 Da). This pattern is representative of alternating disaccharide bases as may be contained in glycoprotein chains and is too small to represent most common cell proteins.

Abundant sulphur-rich material was identified by electron microscopy directed X-ray diffraction. In alcohol dehydrated or freeze-dried tissue after glutaraldehyde fixation, PSG, DCB and EB contained high concentrations of sulphur despite low concentrations of sulphur containing amino acids. Areas of cytoplasm between PSG and areas of stroma in freeze-dried tissues were targeted and failed to reveal any sulphur and were therefore used as control background graphs. Importantly, the presence of sulphur in DCB that had lost eosinophilic staining in routine processing indicated that eosinophilia and sulphur may depend upon the presence of two separate molecules; the first a sulphated glycosaminoglycan the second a cationic protein. Further, sulphur was present at comparably high levels in corpora amylacea and in luminal crystalloids of clear cell carcinomas.

PSG, EB and corpora amylacea were all moderately to strongly PAS positive regardless of tissue preparation. In glutaraldehyde-fixed, freeze-dried preparations, alcian blue (pH=1) weakly stained PSG and strongly stained EB, with staining limited to the brightly eosinophilic rim. Corpora amylacea were alcian blue positive (pH=1 & 2.5). Clear cell carcinomas were consistently negative for mucin with alcian blue (pH=2.5) or STN antibody, a mucin tag seen in most prostate cancers (23). Their granular luminal contents were weakly alcian blue positive (pH=1), as were scattered foci within crystalloids. By contrast, there was intense mucin positivity (STn and Alcian Blue, pH=2.5) in carcinomas with amphiphilic cytoplasm. It consistently filled cancer gland lumens and STn was focally present within malignant cell cytoplasm.

TABLE 2

Histochemical, immunostaining and X-Ray analysis of prostate associated granules (PSG) and extracellular protein deposits

| | Prostate Secretory Granules | Decapitated Cytoplasmic Bodies | Eosinophilic Bodies | Corpora Amylacea | Prostatic Crystalloids |
|---|---|---|---|---|---|
| Eosin | +++ | − | +++ | ++ | +++ |
| PAS | + | − | ++ | ++ | + |
| Alcian Blue (pH 1.0) | ± | − | ++[1] | ++ | +[2] |
| Congo Red | +++ | − | +++ | ++ | +++ |
| Phloxine Tartrazine | ++ | − | +++ | +++ | +++ |
| β2 microglobulin | ± | − | − | ± | − |
| STn Antigen | − | − | − | − | − |
| PSA/PAP | +++[3] | − | − | − | − |
| Sulphur | +++ | +++ | +++ | ++ | +++ |

[1]Outer Rim staining
[2]Amorphous material surrounding crystalloids
[3]Apical PSG
± − Initial focal weak staining, eliminated with avidin-biotin blocking.
+ moderate staining.
++ strong staining.
+++ intense staining PSG, DCB, EB, corpora amylacea and crystalloids all stained strongly with Congo Red and with phloxine tartrazine (Table 2). However, there was no apple green birefringence under polarized light with any of these structures.

Immunostains for PSA, PAP and Keratan Sulphate exclusively stained the PSG of benign glands while in amphiphilic carcinoma it followed in general, the same luminal distribution of cancer associated mucin. Weak immunostaining for β-2 microglobulin was identified in the PSG and corpora amylacea. However, on repeated stains, this apparent immunoreactivity to β-2 microglobulin was significantly reduced or eliminated with the use of avidin-biotin blocking (Dako Corp, Denmark X0590). Immunoreactivity for mucin using anti-STn was negative in all benign epithelial tissues. Keratan sulphate stains identified the PSG, eosinophilic rim of the DCB and CA. This confirmed the identity of the PSG associated GAG protein as Keratan sulphate. Cancer cells were usually weakly stained or failed to stain with Keratan Sulphate.

PSG extracted through a sucrose gradient were confirmed by electron microscopy to be highly concentrated in the 18,000 g extraction. Standard polyacrylamide gel electrophoresis of 18,000 g extractions of benign tissue and cancer tissue identified numerous bands in each group. Western blot preparation using PSA confirmed immunolocalisation to a 33–37 kDa band in all extracts but repeated attempts using β-2 microglobulin failed to recognize any protein fraction. Western bot analysis for Keratan Sulphate confirmed a defined band at 75–80 KDa. Despite multiple efforts, no definite protein bands were seen in gels run from dissolved concretions. Instead, only stained smears were seen suggesting a lack of any sizable pure protein fractions within the prostatic concretions. This pattern however, is frequently seen in gels containing glycosaminoglycans.

Discussion

Since 1779 when Morgagni described the corpora amylacea as the coagulated humour of the prostate (24) little has been known about the nature of the secretory process in prostatic epithelium and its dramatic differences between benign and malignant epithelium. Research in this area has undoubtedly been hindered by the high susceptibility of the morphologic components of the secretory apparatus to severe distortion by routine fixation. Yet in addition, there has been reluctance to consider the exclusive presence of corpora amylacea in the lumens of benign glands and conversely limitation of luminal mucin or crystalloids to cancer as possibly important clues to some of the phenotypic changes accompanying malignant transformation. Much more has been written about the very uncommon presence of crystalloids or mucin in benign gland lumens than about their possible biologic relationship to process in the malignant glands which they are almost invariably associated.

With the aid of careful fixation and tissue processing, we have been able to derive morphologic evidence about the normal prostatic secretory process and its disruption in carcinoma. The prostatic secretory granule (PSG) is a 1 μm, membrane bound structure originating from the Golgi apparatus and containing the bulk of the many different species of prostatic secretory products including PSA, PAP and now a copious amount of GAG protein in the form of Keratan Sulphate. The PSG accumulate in the apical third of the cell, are secreted by a unique apocrine mechanism and are finally dispersed in the gland lumen.

The luminal cytoplasmic compartment (bleb), emptied of its protein enzymes, becomes a decapitated cytoplasmic body (DCB), a partly collapsed, faintly basophilic membrane with remnant cytoplasm. The DCB shrinks to form a sphere with a thickened, brightly eosinophilic surface casing, the eosinophilic body (EB). This structure presumably may dissolve in luminal secretions, but it is also observed that it may adsorb to the surface of the corpus amylaceum and the EB appears to be its chief mechanism for adding bulk and lamellar structure. The loss of eosinophilia within decapitated cytoplasm therefore represents the loss of one of the PSG constituent proteins, likely to represent a cationic protein enzyme. The eosinophilia of the EB rim by contrast is due to a glycoprotein complex. Further, EB previously recognized (9) as rare structures within the prostate devoid of PSA and occurring only in central areas, represented an artefact of standard fixation where their central location protected them from complete elution as evidenced by current glutaraldehyde fixation and freeze-drying techniques.

Endogenous biotin reactivity recognized within the PSG and corpora was greatly enhanced by heat antigen retrieval. Recognition of this activity has previously been confined to the kidney, brain and liver tissue (25) but not prostate gland. Its presence has implications for all immunostains on prostate tissues when using heat retrieval as it can produce falsely positive results. Accordingly, β-2 microglobulin positivity was almost completely eliminated by avidin-biotin blocking. The diagnostic accuracy of the polyclonal serum used in this and previous studies (12) is further questioned by a negative result on repeated western blotting, a technique not previously used in the evaluation of prostatic β-2 microglobulin. The concept that corpora amylacea arise from urinary proteins (12) has been discounted by this observation.

The corpora amylacea were found to be composed of more carbohydrate than protein (monosaccharide/amino acid—2:1) and its high concentrations of glucosamine, and galactose parallels the sugar and sulphate content of cytoplasmic PSG confirming the histological findings that the latter contributes to the formation of the former. The carbohydrate and sulphate content is typical of a glycosaminoglycan and from the amino acids present in the protein backbone, is entirely consistent with Keratan sulphate (26). Glycosaminoglycans are responsible for the formation of protease granules in other well characterised biological systems including leucocytes, basophils and mast cells where the anionic proteoglycan binds and temporarily stabilizes the cationic proteases (27).

In prostatic adenocarcinomas, with few exceptions and whatever the grade or cytoplasmic type, the entire secretory apparatus was absent; neither PSG nor DCB were found. An inability to form corpora amylacea arises inexorably from this fact. In the usual moderately differentiated cancers with dark cytoplasm (Gleason grade 3), luminal mucin is often abundant, but there is no evidence of its cytoplasmic precursor. Mucin does not appear to be derived from distortion of benign cell carbohydrate processing. PSA and PAP are both diffusely cytoplasmic and luminal plasma membrane concentrated. It can be speculated that these enzymes previously linked to anionic glycosaminoglycans are in transformed cells somehow linked to mucin metabolism in a novel membrane transport process.

Fields of amphiphilic Grade 3 cancer often abut or surround clear-cell carcinoma foci. Their cytoplasm is superficially identical to that of normal benign epithelium, but they are filled with lipid vacuoles rather than PSG[1] and hence represent an unique differentiation pathway. The presence of small numbers of PSG and focal Keratan Sulphate staining in some clear cells indicates that to a minor degree the normal secretory pathway is still open. Perhaps it is significant that in clear cell carcinoma gland lumens with higher PSG concentrations in surrounding cells, eosinophilic sulphur containing crystalloids are especially common. Perhaps crystalloids represent a remnant product of normal secretion, with preservation of the cationic strongly eosinophilic PSG protein, which has crystallized in an altered environment. The usually high sulphur content of the glycosaminoglycan of the PSG pathway has also been identified in crystalloids (11) and crystalloids share similar histochemical staining patterns with PSG.

As GAGs such as Keratan Sulphate usually complex with specific proteins, the Keratan Sulphate associated protein core may represent a secreted product of the PSG which may be useful in both the diagnosis and therapy of prostatic conditions.

EXAMPLE 4

Prostate Secretory Granules (PSG) as a Marker of Prostatitis

Chronic non-infective prostatitis is a poorly defined disease process whose aetiology is currently unknown. Serum from a group of four men with histologically proven prostatitis (granulomatous) was subjected to Western blot analysis to identify any possible antibody the PSG or its components. A group of normal males and females were used as controls. Early results indicate the presence of an auto-antibody against a protein component of PSG which has a weight of between 55 and 65 KDa. this antibody was not detected in normal controls. This may prove a useful diagnostic marker in diagnosis of chronic prostatitis.

EXAMPLE 5

Chromophobe Renal Carcinoma

Chromophobe cell renal carcinoma is a distinct tumour type with unique morphologic and cytogenetic features (28–32). The major histological feature, which characterizes these carcinomas, is their voluminous cell cytoplasm that has a pale finely reticular quality and contrasts with well-defined cell borders. An eosinophilic variant is also recognised in which tumour cells contain an additional complement of mitochondria. Distinction from conventional renal carcinoma is totally dependent on the identification of these subtle features in routinely stained sections and the diagnosis is only then confirmed by special stains and/or electron microscopy. These tumours unlike conventional (clear cell) renal cell carcinomas contain abundant mucopolysaccharide that reacts positively with Hale's colloidal iron (29), they lack neutral fat, and although irnmunoreactive for cytokeratin, they are negative for vimentin staining. Ultrastructurally the tumour is characterised by numerous cytoplasmic micro-vesicles, thought to arise from outpouchings of the cytoplasmic mitochondria (33,34). These tumours appear to have a significantly more favourable outcome when compared with conventional clear or granular cell (30,31,35).

Case Report

A 71-year-old male presented with recent onset abdominal discomfort and an incidental 4 cm mass was identified on CT scan in the upper pole of the left kidney. Past medical history included a previous diagnosis of prostatic carcinoma for which the patient had received external beam radiation. At this time there was no evidence of prostatic tumour recurrence and serum PSA was 0.1 ng/ml (normal range <4 ng/ml).

Gross Features

Following a left radical nephrectomy the fresh specimen was bisected and a uniform tan colored partly cystic tumour was identified arising from the superficial cortex of the upper pole. The tumour appeared partly encapsulated and did not involve the renal vessels.

Materials and Methods

Tumour tissue was fixed in both 4% buffered formaldehyde well as "Solufix" (Tissue Technologies, Australia) a commercial tissue fixative, while frozen unfixed tissue was sectioned and stained for neutral fat using Sudan IV. Processed tissues (both Solufix and formaldehyde fixed) were cut at 4 μm for routine haematoxylin and eosin stains, PAS, Pearls Prussian Blue, Von Kossa as well as stains for mucopolysaccharides (Hale's colloidal iron). Immunostains for Vimentin (Dako Corp, Denmark, 1:100) were performed and cryostat sections were stained for lipid with Sudan IV. For electron microscopy, thin sections (60–90 nm) were stained with uranyl acetate and lead citrate and were examined in a Phillip's 410LS Transmission Electron Microscope at 80 KV. X-ray microanalysis was also carried out with an EDAX detection system (Moran Scientific Software, Australia).

DNA Isolation

To isolate DNA from tumour tissue and normal kidney tissue, 20 μm paraffin sections were cut, dewaxed in xylene and then DNA was prepared as previously described (36). Loss of heterozygosity was determined by PCR amplification of polymorphic microsatellite markers and gel electrophoresis (37). Markers used in this study were against regions previously reported as being useful in the differential diagnosis of renal cell (38). These included D1S2883 (chromosome 1), D2S202 (2q32), D3S1675 (3p), D3S1497 (3p22–3p21.3), D3S1514 (3p21–3p14.2), D3S1447 (3p21), D3S1478 (3p21.3–3p21.2), D3S1581 (3p21.2), D6S305 (6q27), D10S1239 (10q23–10q24), D13S317 (13q22), D17S559 (17p13), D17S855 (17q12–17q21), D21S267 (21q22.1–21q22.3).

Results

Routine formaldehyde fixed tissue confirmed a tumour growing in solid sheets as well as focally having a tubuloalveolar pattern. Tumour cells had clear bulky cytoplasm, moderate nuclear atypia and indistinct cell membranes. In contrast, tumour tissue fixed in Solufix demonstrated good preservation of cell cytoplasm that had a fine reticular quality contrasting with sharply defined cell borders. Dark smudged nuclei seen in the formaldehyde fixed tissue were not identified in material preserved in Solufix. In contrast, nuclei were clear with distinctly clumped chromatin. As .cell membranes were sharply focused, the voluminous cytoplasm created a characteristic "plant cell like" appearance, a feature not easily recognised in routine formaldehyde fixed sections. An unusual feature seen in all sections was the formation of numerous psammoma bodies. These seemed to arise from the "center" of tubulo-alveolar structures, which frequently contained eosinophilic material studded with small flecks of calcium. Histochemical and immunostains were similar in both Solufix and formalin fixed samples. Stains for Hale's colloidal iron was strongly positive in the cell cytoplasm and stained the "central" amorphous deposits and emerging psammoma bodies. These structures also stained strongly with Prussian blue stain (Pearls) and Von Kossa confirming their ferrous and calcium content. PAS stain confirmed occasional focal positivity for glycogen and immunostains for vimentin were negative in all tumour cells. Cryostat sections were negative for neutral fat (Sudan IV).

Electron Microscopy

The tumour consisted of closely apposed polygonal cells often arranged in "tubule-like" structures. A prominent basal lamina surrounded each cluster of cells while small stunted microvilli projected into the narrow intercellular space as well as in lumen-like spaces. The "central" proteinacious material that was noted on light microscopy to form psammoma bodies was recognised as a primarily stromal/ basement membrane structure, which contained electron dense granular material. This material ranged in size from 25–280 nm in diameter and was occasionally observed as a fibrillar feather-like structure. Larger granules were also identified and found on EDAX analysis to contain significant peaks for iron, calcium and phosphate confirming the light microscopic findings. The main ultrastructural feature of the tumour cells were the presence of vacuolar and vesicular structures in the cytoplasm ranging in size from 500–1600 nm. They consisted of a closed smooth membrane and were either round, ovoid or irregular in shape and a small proportion contained "inner vesicles" measuring 150–300 nm in diameter. The vesicular membranes were always smooth and ribosomes were never seen on their surface.

Molecular Biological Assessment No loss of heterozygosity (LOH) was observed at D3S1447. The patient was homozygous at D3S1675, D3S1497, D3S1514, and D3S1478. LOH at chromosome 3p is commonly observed in conventional (clear cell) non-papillary renal cell carcinomas. No LOH was observed at D1S2883, D2S202, D6S305, D10S1239, D13S317, D17S559 or D21S267. The patient was homozygous at D17S855. LOH at these loci is also commonly observed in chromophobe renal cell carcinomas and occasionally oncocytoma.

Discussion

Chromophobe renal carcinoma has a significantly better prognosis than conventional renal carcinoma (clear cell type) therefore making it mandatory that distinction be made in each case. Although the gross appearance is often suggestive, diagnosis rests with its characteristic light microscopic appearance. The abundant reticular cytoplasm with distinct cell borders often provides the clue to embark on confirmatory histochemical and immunostains or in selected cases, electron microscopy. In this case, these light microscopic features were not obvious in formaldehyde fixed tissue and were only noted after fixation in Solufix. The histochemistry, immunostains and electronnmicroscopic features all strongly support the diagnosis of chromophobe carcinoma and although the molecular markers do not identify any of the many possible markers of chromophobe carcinoma, they also do not support the diagnosis of a conventional "clear cell" carcinoma.

A feature of this tumour is the presence of numerous psammoma bodies. These are often seen in papillary renal carcinoma (39) and occasionally in oncocytoma (7%) (30). The mechanism of psammomatous calcification is controversial and the accepted concept of origin from necrotic papilla has been questioned by the presence of hydroxyapatite suggesting intracytoplasmic evolution of psammoma bodies (40). In this case origin appears to be within the stroma adjacent to tumour cells in which accumulation of mucopolysaccharides, calcium ions and haemosiderin initiates the evolution of the psmmoma body. The association of psammoma bodies with haemosiderin pigment has not been previously described and may be important factor in this unusual form of calcification.

In summary this case represents a renal tumour that has the features of a chromophobe carcinoma, but would have been classified as conventional "clear cell" carcinoma[24] if fixed only in formaldehyde. After fixation in "Solufix" cytological features suggestive of chromophobe renal carcinoma were easily appreciated. As formaldehyde is the mainstay of tissue fixation it is highly likely that many other renal tumour variants have been designated conventional "clear cell" renal cell carcinoma without further investigation. As the classification of renal carcinoma is incomplete and constantly changing (41) variant tumours such as this case require identification not only to refine and improve these tumour divisions but also because of their prognostic differences. Future fixation of at least small samples of tumour in Solufix may avert future misdiagnosis with their subsequent prognostic implications.

EXAMPLE 6

Characterisation of Keratan Sulphate-Associated Protein

Materials and Methods

1. Benign protatic tissue was homogenised and then diluted with an equal volume of buffered sucrose.
2. The homogenate was centrifuged at 750×g for 10 minutes at 4° C.
3. The supernatant was collected and each 3 ml was layered onto a discontinuous sucrose gradient consisting of 3 ml each of 20%, 40% and 60% (w/v) sucrose buffered with 10 mM Tris phosphate.
4. The tubes were centrifuged at 20,000 rpm for 3hr at 4° C. in a Beckman SW41 rotor.
5. Fractions were collected from above the 20% sucrose layer (supernatant) and the interaces between the 20% and 40% (interphase 1) and the 40% and 60% (interphase 2) layers.
6. Material from interphase 2 was recognised by electron microscopy to contain intact PSGs.

Results

Interphase 2 material was run on a standard PAGE gel and western blot analysis confirmed keratan sulphate binding to several major protein bands. The largest of these (70–75 kD) was cut from the gel.

EXAMPLE 7

Effect of Keratan Sulphate on Immune Responses

Materials and Methods

Figure 2:
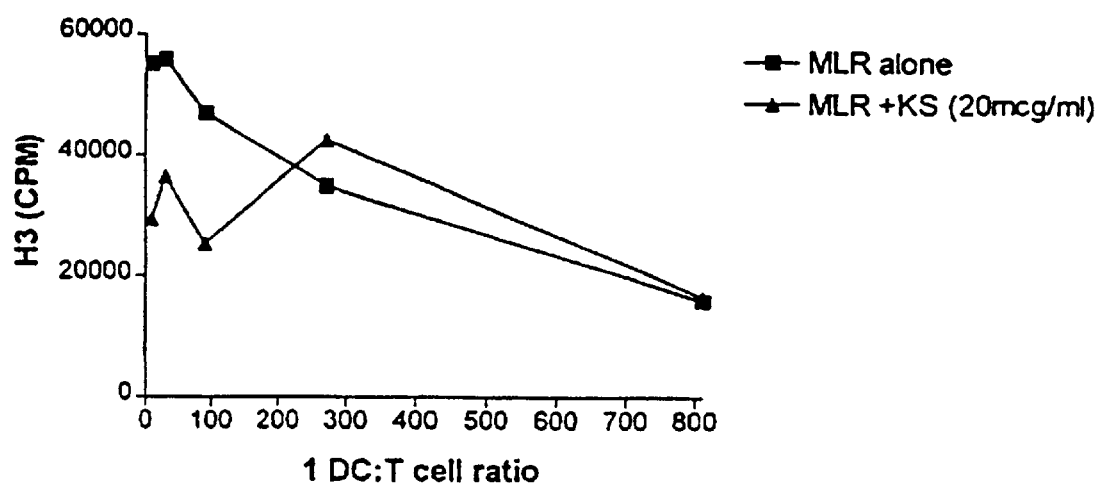
FIG. 2 Effect of keratan sulphate on a mixed lymphocyte reaction.
Figure 2:
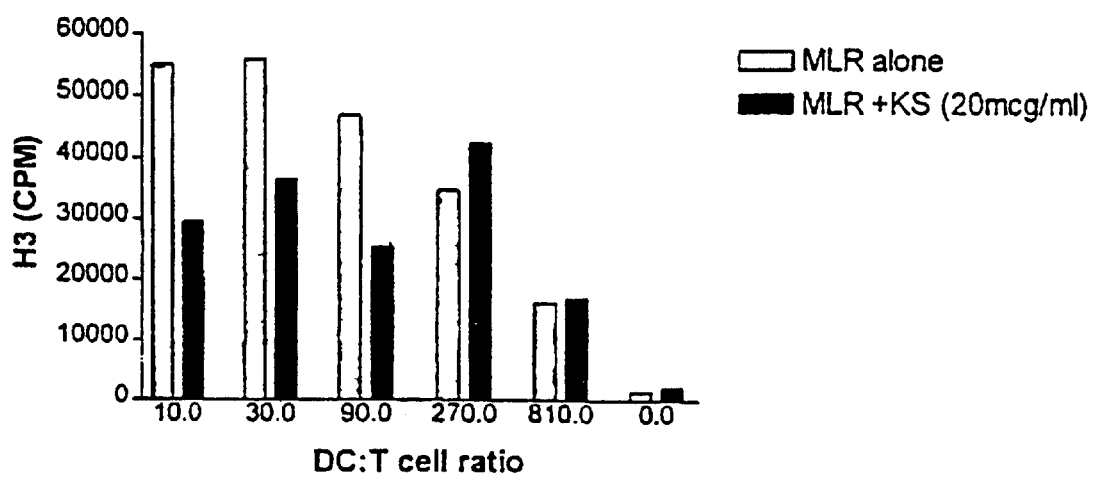

The function of keratan sulphate in prostate tissue is unknown. It is known, however, that GAG compounds are important in the prevention of autoimmune bonne diseases (forms of arthritis). In order to determine whether keratan sulphate may have an immune regulatory effect it was assessed by intorducing it into a mixed lymphocyte reaction. At a concentration of 20 μg/ml, a reduction of 50% was observed at lymphocyte ratios of 10, 30 and 90:1. At markedly diluted lymphocyte ratios of >270:1 no effect was evident (see FIG. 2).

These results confirma significant inhibitory effect of keratan sulphate on the immune response. This may be important in normal prostate function, maintaining viability of sperm and for fertility.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

1. McNeal J E, Prostate. In: Sternberg S S, ed. Histology for pathologists, 2nd Edition, Chapter 42, Philidelphia-New York, Raven Press, 997–1017, 1997.
2. Epstein J I, Prostate biopsy interpretation, Second Edition, Philadelphia-New York, Lippincott-Raven Press, 1–12, 87–133, 1995.
3. Epstein J I. Diagnostic criteria of limited adenocarcinoma of the prostate on needle biopsy. *Hum Pathol* 26: 223–229, 1995.
4. Gleason D F. The Veterans Administration Co-Operative Urological Research Group; histological grading and clinical staging of prostatic carcinoma. In Tannenbaum M ed., Urological Pathology. Philadelphia: Lea & Febinger, 171–197, 1977.
5. McNeal J E. Redwine E A. Freiha F S. Stamey T A. Zonal distribution of prostatic adenocarcinoma. Correlation with histologic pattern and direction of spread. *Am J Surg Pathol* 12(12): 897–906, 1988.
6. Brandes D Lesions of the prostate, In G Hill ed Uropathology, New York, Churchill Livingstone, 1989.
7. Cina S J, Epstein J I. Adenocarcinoma of the prostate with atrophic features. *Am J Surg Pathol* 21(3): 289–295, 1997.
8. de Vries C R, McNeal J E, Bensch K. The prostatic epithelial cell in dysplasia: an ultrastructural perspective. *Prostate* 21: 209–221, 1992.
9. Cohen R J, Verhaart M J S, Taylor L F. Intracytoplasmic inclusions in benign prostatic epithelium. *Arch Pathol Lab Med* 118: 1030–1031, 1994.
10. Drachenberg C B. Papadimitriou J C. Prostatic corpora amylacea and crystalloids: similarities and differences on ultrastructural and histochemical studies. *Journal of submicroscopic Cytology & Pathology.* 28(2):141–50, 1996 April.
11. Del Rosario A D. Bui H X. Abdulla M Ross J S. Sulfur-rich prostatic intraluminal crystalloids: a surgical pathologic and electron probe x-ray microanalytic study. *Human Pathology.* 24(11):1159–67, 1993.
12. Cross P A. Bartley C H. McClure J. Amyloid in prostatic corpora amylacea. *Journal of Clinical Pathology.* 45 (10): 894–7, 1992.
13. Jiang, J. D., Wang, Y., Roboz, J., Strauchen, J., Holland, J. F. and Bekesi, J. G. Inhibition of microtubule assembly in tumour cells by 3-bromoacetylamino benzoyl urea, a new cancericidal compound. *Cancer Res.* 58:2126–2133, 1998.
14. Niwa, J., Minase, T., Mori, M. And Hashi, K. Immunohistochemical, electron microscopic, and morphometric studies of human prolactinomas after short term bromocriptine treatment. *Surg. Neurol.* 28(5): 339–344, 1987.
15. Bass D A. Lewis J C. Szejda P. Cowley L. McCall C E. Activation of lysosomal acid phosphatase of eosinophil leukocytes. *Lab Investig* 44(5):403–409, 1981.
16. Egesten A, Calafat J, Weller P F, Knol E F, Janssen H, Walz T M, Olsson. Localization of granule protein in human eosinophil bone marrow progenitors. *Internat Arch Allergy Imunol* 114: 130–138, 1997.
19. Grey E, Edgar S G, Cohen R J. Immunohistochemical detection of PSA antigen using a monoclonal antibody and polyclonal serum: a quantitative assessment using image analysis. *Brit J Urol* 78:104–108 1996.
20. Wolff J M, Borchers H, Effert P J, Habib F K Jakse G. Free-to-total prostate-specific-antiigen serum concentrations in patients with prostate cancer and benign prostatic hyperplasia. *Brit J Urol* 78: 409–413, 1996.
21. Epstein J I. Adenosis (atypical adenomatous hyperplasia): Histopathology and relationship to carcinoma. *Pathol Research & Practice* 191(9): 888–898, 1995.

22. Gaudin P B. Epstein J I. Adenosis of the prostate: Histologic features in needle biopsy specimens. *Am J Surg Pathol* 19(7): 737–747, 1995.
23. Kuwabara H, Uda H, Takenaka I. Immunohistochemical detection of sialosyl-Tn antigen in carcinoma of the prostate. *British Journal of Urology* 1997;80:456–459.
24. Prather G, Skinner D. Prostatic corpora amylacea. *Journal of Urology* 1956;76:107–114.
25. Bussolati G, Gugliotta P, Volante M, Pace M, Papotti M. Retrieved endogenous biotin: a novel marker and a potential pitfall in diagnostic immunohistochemistry. *Histopathology* 1997; 31(5):400–407.
26. Parmley R T Hurst R E, Takagi M, Spicer S S, Austin R L. Glycosaminoglycans in human neutrophils and leukemic myeloblasts: ultrastructural, cytochemical, immunogenic and biochemical characterization. *Blood* 1983; 61(2): 257–266.
27. Fischer D C. Henning A. Winkler M. Rath W. Haubeck H D. Greiling H. Evidence for the presence of a large keratan sulphate proteoglycan in the human uterine cervix. [journal Article] *Biochemical Journal*. 1996; 320 (Pt 2):393–399.
28. Bonsib S, Lager D: Chromophobe cell carcinoma: analysis of five cases. *American Joumcal of Surgical Pathology* 14:260–267, 1990.
29. Tickoo S, Amin M, Zarbo R: Colloidal iron staining in renal epithelial neoplasms, including chromophobe renal cell carcinoma: emphasis on technique and patterns of staining. *American Journal of Surgical Pathology* 22:419–424, 1998.
30. Cochand-Priollet B, Molinie V, Bougaran J et al: Renal chromophobe cell carcinoma and oncocytoma. A comparative morphologic, histochernical, and immunohistochemical study of 124 cases. *Archives of Pathology & Laboratozy Medicine* 121:1081–1086, 1997.
31. Crotty T, Farrow G, Lieber M: Chromophobe cell renal carcinoma: clinicopathological features of 50 cases. *Journal of Urology* 154:964–967, 1995.
32. Billis A, Carvalho R, Magrini E et al: Chromophobe renal cell carcinoma: clinicopathological study of 7 cases. *Ultrastructural Pathology* 22:19–26, 1998.
33. Thoenes W, Storkel S, Rumpelt H-J et al: Chromophobe cell renal carcinoma and its variants—a report on 32 cases. *Journal of Pathology* 155:277–287, 1988.
34. Erlandson R, Reuter V: Renal tumor in a 62-year-old male. *Ultrastructural pathology* 12:561–567, 1988.
35. Renshaw A, Henske E, Loughlin K et al: Aggressive variants of chromophobe renal cell carcinoma. *Cancer* 78:1756–1761, 1996.
36. Turbett G R, Barnett T C, Dillon E K et al: A single-tube protocol for the extraction of DNA or RNA from paraffin-embedded tissues using a starch-based adhesive. *BioTechniques* 20:846–853, 1996.
37. McCulloch R, Sellner L, Papadimitriou J et al: The incidence of microsatellite instability and loss of heterozygosity in fibroadenoma of the breast. *Breast Cancer Research and Treatment* 49:165–169, 1998.
38. Bugert P, Kovacs G: Molecular Differential diagnosis of renal cell carcinomas by microsatellite analysis. *American Journal of Pathology* 149:2081–2088, 1996.
39. Delahunt B, Eble J: Papillary renal cell carcinoma: a clinicopathologic and immunohistochemical study of 105 tumors. *Modern Pathology* 10:537–544, 1997.
40. Murayama H, Kamio A, Imai T et al: Gastric carcinoma with psammomatous calcification: report of a case, with reference to calculogenesis. *Cancer* 49:788–796, 1982.
41. Kovacs G, Akhtar M, Beckwith B et al: The Heidelberg classification of renal cell tunouris. *Journal of Pathology* 183:131–133, 1997

What is claimed is:

1. A method of diagnosing prostate pathology in a subject which method comprises
   (i) fixing a sample of prostate tissue from the subject in a fixative which produces substantially identical cytoplasmic fixation to that produced by glutaraldehyde at a concentration of at least 2.0%; and
   (ii) analysing the sample for the presence of at least one structure selected from the group consisting of prostate secretory granules (PSG), eosinophilic bodies (EB), decapitated cytoplasmic bodies (DCB), corpora amylacea (CA), or the contents of any one or more of these structures.

2. A method as claimed in claim 1 in which the prostate pathology is prostatitis or prostate cancer.

3. A method as claimed in claim 1 in which the protate pathology is prostate cancer.

4. A method as claimed in claim 1 in which the analysis in step (ii) is performed by light microscopy.

5. A method as claimed in claim 4 in which the tissue is stained with haematoxylin and eosin.

6. A method as claimed in claim 1 in which the analysis in step (ii) comprises electron microscopy.

7. A method as claimed in claim 1 in which the analysis in step (ii) comprises immunostaining.

8. A method as claimed in claim 1 in which the fixative produces substantially identical cytoplasmic fixation to that produced by glutaraldehyde at a concentration of between 2.5% and 6%.

9. A method as claimed in claim 1 in which the fixative comprises glutaraldehyde at a concentration of between 2.5% and 6%.

10. A method as claimed in claim 1 in which the fixative composition comprises an aqueous solution of glutaraldelhyde at a concentration of between 2.5% and 6%, a metallic salt and a buffer stabiliser, the composition having a pH of between 5.7 and 5.75.

11. A method as claimed in claim 10 in which the amount of glutaraldehyde ranges from about 3.5% to about 5% by volume of the composition.

12. A method as claimed in claim 10 in which the metallic salt is selected from the group consisting of zinc sulphate, copper sulphate, barium sulphate, cobalt chloride, barium chloride, potassium chloride, mercuric chloride and lead chloride.

13. A method as claimed in claim 12 in which the metallic salt is zinc sulphate.

14. A method as claimed in claim 10 in which the concentration of the metallic salt raiiges from 3.0 to 20.0 g/l.

15. A method as claimed in claim 10 in which the buffer comprises one or more acetic acid compounds.

16. A method as claimed in claim 15 in which the buffer stabilizer comprises sodium acetate at a concentration of about 0.2M and acetic acid at a concentration of about 0.2M.

17. A method as claimed in any one of claims 10–16 in which the fixative further compnrises one or more components selected from the group consisting of:

Detergents,

Azone (laurocaprame 1-dodecylazacyclo-hepton-2-one) 3% w/v or 1-geranylazacyclohepton-2-one 3% w/v, Liposomes, Sodium taurocholate 40–0.25 $\mu$M Solution C24 (polyoxyethene-24-cholesterol-ether), Polyethylene glycol 200 dilaurate (0.1–10%), Menthol 1% w/v, Mercaptoethanol (0.0025%),
Glycerol trioleate,
Terpene penetration enhancers,
Medium chain fatty acids,
Trichloroactic acid (0.5–5.0%),
Metallic salts,
Dimethylsulfoxide (0.1–20%),
Mono and disaccharides,
Urea, and
Methyl salicylate.

* * * * *

UNITED STATES PATENT AND TRADEMARK OFFICE
CERTIFICATE OF CORRECTION

PATENT NO. : 6,677,157 B1  Page 1 of 1
DATED : January 13, 2004
INVENTOR(S) : Ronald J. Cohen It is certified that error appears in the above-identified patent and that said Letters Patent is hereby corrected as shown below:

Title page,
Item [57], ABSTRACT,
Line 7, replace "o" with -- or --.

Column 26,
Line 49, replace "raiges" with -- ranges --.

Signed and Sealed this

Sixth Day of July, 2004

*JON W. DUDAS*
*Acting Director of the United States Patent and Trademark Office*